United States Patent [19]

Gurske

[11] 4,321,121

[45] Mar. 23, 1982

[54] ELECTROPHORETIC TECHNIQUE FOR SEPARATING LACTATE DEHYDROGENASE ISOENZYMES AND IMPROVED ELECTROPHORETIC GEL FOR USE THEREIN

[75] Inventor: William A. Gurske, Placentia, Calif.

[73] Assignee: Beckman Instruments, Inc., Fullerton, Calif.

[21] Appl. No.: 226,571

[22] Filed: Jan. 19, 1981

[51] Int. Cl.$^3$ ............................................. G01N 27/26
[52] U.S. Cl. ........................... 204/180 G; 204/299 R; 536/3; 23/230 B
[58] Field of Search ...................... 204/180 G, 299 R; 536/3, 4, 5, 6; 260/112 B, 122

[56] References Cited

U.S. PATENT DOCUMENTS

| | | | |
|---|---|---|---|
| 3,527,712 | 9/1970 | Renn et al. | 204/180 G X |
| 3,947,352 | 3/1976 | Cuatrecasas et al. | 204/122 X |
| 3,956,272 | 5/1976 | Tixier | 536/3 X |
| 3,956,273 | 5/1976 | Guiseley | 536/3 X |
| 3,959,251 | 5/1976 | Porath et al. | 536/3 X |

*Primary Examiner*—Arthur C. Prescott
*Attorney, Agent, or Firm*—R. J. Steinmeyer; J. E. Vanderburgh; Robert S. Frieman

[57] ABSTRACT

An electrophoretic gel of the type comprising a polysaccharide. The electrophoretic gel is characterized in that it further comprises either an acid polysaccharide and salts thereof, wherein the acid moiety of the acid polysaccharide comprises at least one carboxyl group and/or a galatomannan polysaccharide.

An improved electrophoretic technique for assaying the relative distribution of lactate dehydrogenase isoenzymes of the type wherein a sample to be assayed is applied to an electrophoretic gel and the electrophoretic gel is electrophoresed. The electrophoretic technique is characterized in that the above described electrophoretic gel is employed therein.

91 Claims, 4 Drawing Figures

ELECTROPHORETIC TECHNIQUE FOR SEPARATING LACTATE DEHYDROGENASE ISOENZYMES AND IMPROVED ELECTROPHORETIC GEL FOR USE THEREIN

BACKGROUND OF THE INVENTION

1. Field of the Invention

The instant invention pertains to an electrophoretic technique for separating lactate dehydrogenase isoenzymes and to an electrophoretic gel for use therein.

2. Description of the Prior Art

Electrophoretic techniques for separating lactate dehydrogenase (LD) isoenzymes and electrophoretic gels for use therein are well known to those skilled in the art. Cawley, *Electroporesis and Immunoelectrophoresis*, Little, Brown and Company, Boston, Mass. (1969). In general, electrophoretic gels employed for separating LD isoenzymes are of the type comprising a polysaccharide. A buffer having a basic pH is also commonly present in these electrophoretic gels.

Typical polysaccharides employed in prior art electrophoretic gels include, but are not limited to, starch, cellulose acetate, agar, agarose, and combinations thereof.

Typical buffers having a basic pH employed in prior art electrophoretic gels include, but are not limited to, the basic pH buffers which are set forth in Table I of Cawley, supra, pp. 331–332.

One problem present in a basic prior art electrophoretic technique for separating LD isoenzymes is that, as shown in FIG. 1, the symmetry of the $LD_1$ band does not correspond to the other four LD bands in that there is a shoulder or bump at the leading edge of the $LD_1$ band.

Accordingly, it would be very desirable to have an electrophoretic technique for the separation of LD isoenzymes wherein the symmetry of the $LD_1$ band is improved to correspond to the other four LD bands.

SUMMARY OF THE INVENTION

In accordance with the present invention there is provided an improved electrophoretic technique for separating LD isoenzymes wherein the symmetry of the $LD_1$ band is improved to correspond to the other four LD bands. The electrophoretic technique of this invention is of the type wherein a sample to be assayed is applied to an electrophoretic gel and the electrophoretic gel is electrophoresed. The improved electrophoretic technique of the instant invention is characterized in that a novel electrophoretic gel is employed therein. This electrophoretic gel is of the type comprising a polysaccharide. A buffer having a basic pH can optionally be present therein. The electrophoretic gel is characterized in that it further comprises either an acid polysaccharide and the salts thereof, wherein the acid moiety thereof comprises at least one carboxyl group and/or a galatomannan polysaccharide. The acid polysaccharide as well as the salts thereof and the galatomannan polysaccharide, when incorporated into the electrophoretic gel either separately or in combination, enables one to obtain an $LD_1$ band having improved symmetry.

Still other features and attendant advantages of the present invention will become apparent to those skilled in the art from a reading of the following detailed description of the preferred embodiments.

DESCRIPTION OF THE PREFERRED EMBODIMENTS

Figure 1:
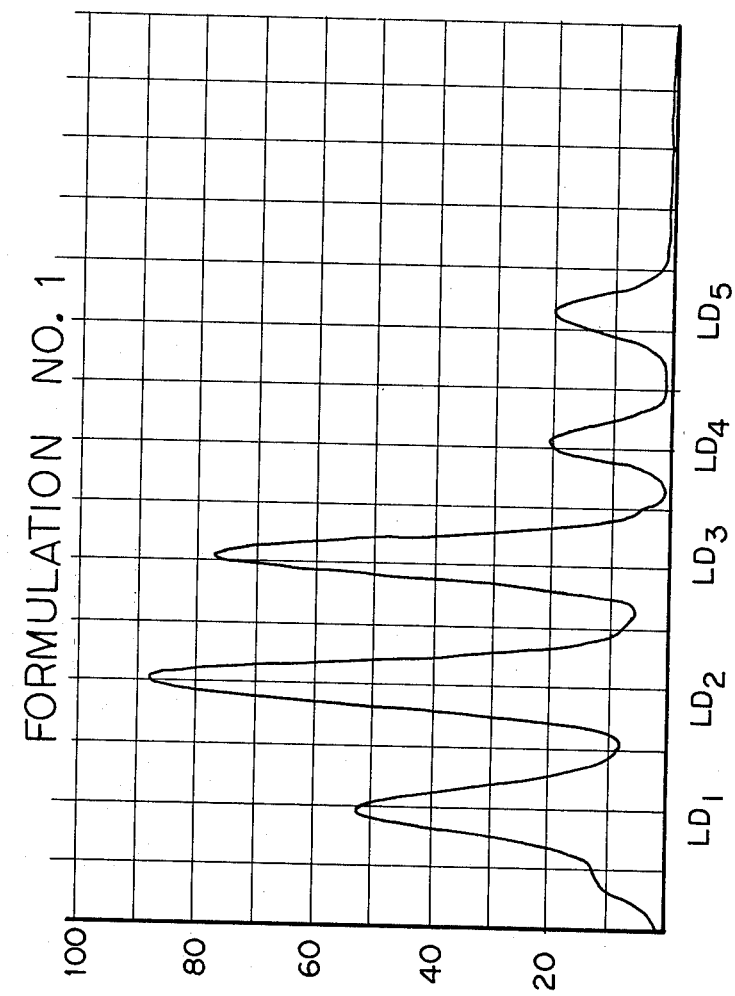
FIG. 1 is a scan of an LD isoenzyme pattern showing a shoulder or bump at the leading edge of the $LD_1$ band.
Figure 2:
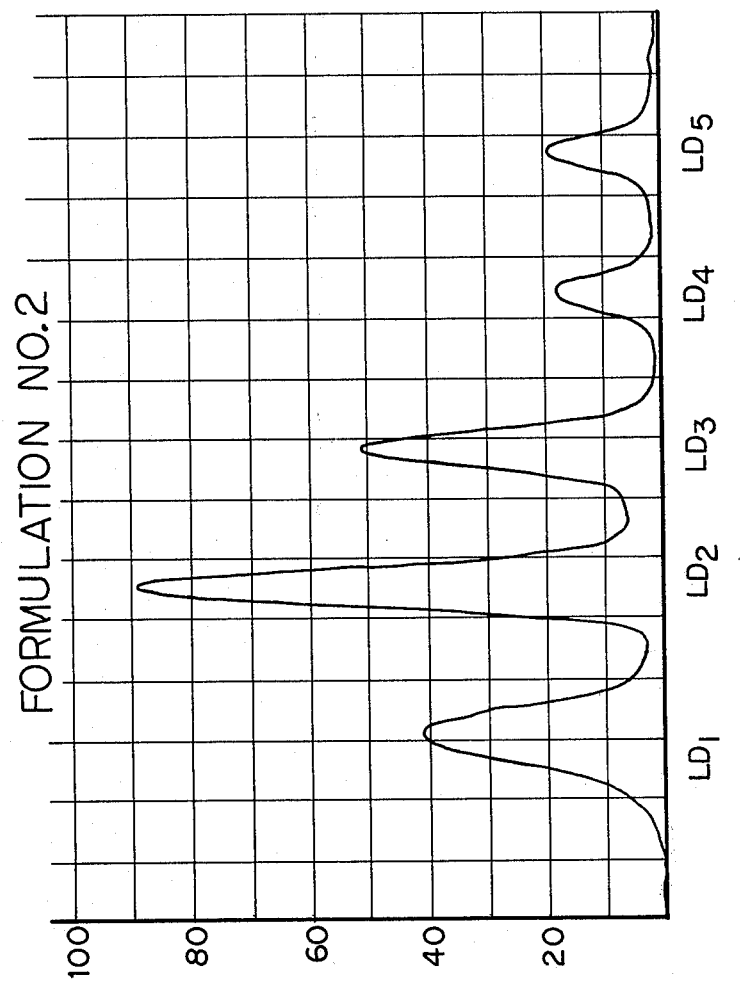
FIG. 2 is a scan of an LD isoenzyme pattern showing a greatly reduced shoulder or bump at the leading edge of the $LD_1$ band.
Figure 3:
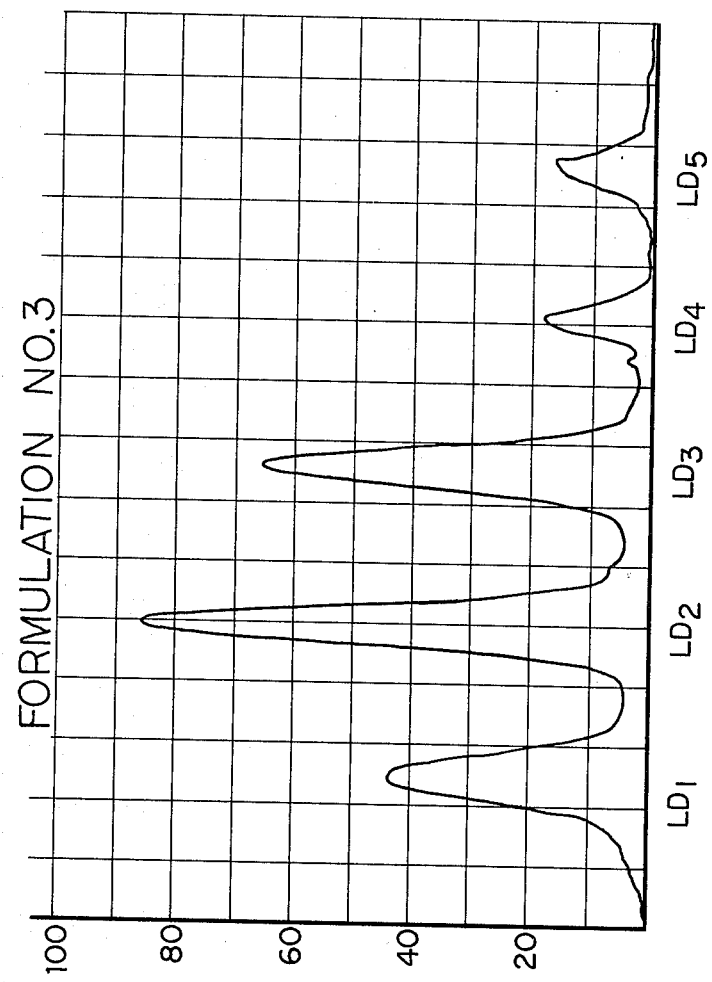
FIG. 3 is a scan of an LD isoenzyme pattern showing a greatly reduced shoulder or bump at the leading edge of the $LD_1$ band.
Figure 4:
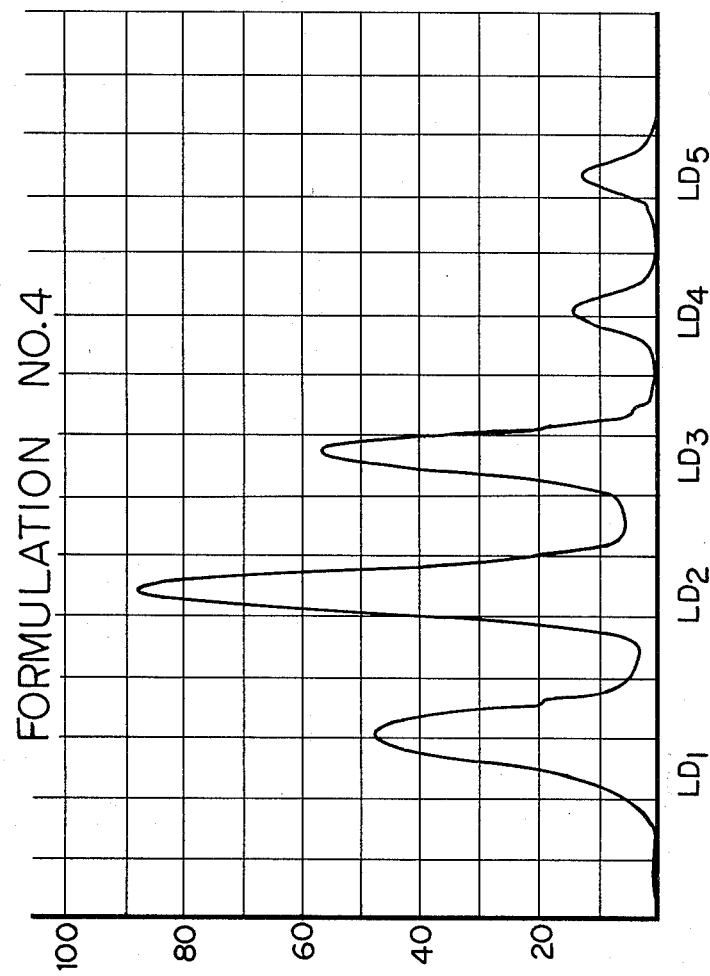
FIG. 4 is a scan of an LD isoenzyme pattern wherein the shoulder or bump is completely eliminated from the leading edge of the $LD_1$ band.

Acid polysaccharides capable of use in the instant invention include, but are not limited to, arabic acid, tragacanth acid, kahya acid, alginic acid, pectic acid, and linseed acid. The preferred acid polysaccharide is arabic acid.

Salts of acid polysaccharides capable of use in the instant invention include, but are not limited to, the sodium, potassium, calcium, and magnesium salts thereof. Examples of such acid polysaccharide salts include, but are not limited to, arabic gum acid, tragacanth gum acid, khaya gum acid, alginic gum acid, pectic gum acid, and linseed gum acid.

Galactommannan polysaccharides capable of use in the instant invention include, but are not limited to, guar gum and locust beam gum. The preferred galactomannan polysaccharide is guar gum.

Polysaccharides which can preferably be employed in the electrophoretic gel of the instant invention are agar and agarose. The agarose can be either low electroendosmosis agarose, medium electroendosmosis, or high electroendosmosis agarose. More preferably, the polysaccharide employed in the electrophoretic gel of the instant invention is high electroendosmosis agarose.

Preferably, the buffer employed in the instant invention has a pH of about 7 to about 10. More preferably the buffer has a pH of about 8 to about 9.

The electrophoretic gel of the instant invention can optionally further comprise a preservative agent. Typical preservative agents include, but are not limited to, antibiotics, halogenated organic compounds, and inorganic compounds. One readily available preservative agent capable of use herein is sodium azide.

The electrophoretic gel of the instant invention can also optionally contain an alkylpolyol having 2 to 6 carbon atoms and 2 to 4 hydroxyl groups. Suitable alkypolyols which can be used herein include, but are not limited to, ehtylene glycol, propanediol, butanediol, pentanediol, and glycerol. Preferably, the alkylpolyol has 2 to 4 carbon atoms.

The exact concentrations of the various constituents employed in the electrophoretic gel of the present invention are not critical. However, in one embodiment of the instant invention, the electrophoretic gel preferably comprises from about 0.4 to about 1.5 percent weight/volume high electroendosmosis agarose; from about 0.01 to about 2 percent weight/volume arabic acid; up to 20 percent volume/volume ethylene glycol; up to 0.5 percent weight/volume sodium azide; and a buffer having a pH of from about 7 to about 10. More preferably, the electrophoretic gel of this embodiment of the instant invention comprises from about 0.7 to about 1.2 percent weight/volume high electroendosmosis agarose; from about 0.5 to about 1 percent weight/volume arabic acid; from about 1 to about 10 percent volume/weight ethylene glycol; from about 0.05 to about 0.15 percent weight/volume sodium azide; and a buffer having a pH of from about 8 to about 9. Optimally, the electrophoretic gel of this embodiment of the instant invention comprises about 1 percent weight/volume high electroendosmosis agarose; about 0.75 percent weight/volume arabic acid; about 5 percent volume/volume ethylene glycol; about 0.1 percent weight/volume sodium azide; and a buffer having a pH of about 8.2 and comprising about 0.3 percent weight/volum aspartic acid; about 0.4 percent weight/volume bicine; about 0.3 percent weight/volume sodium barbital; and about 0.4 percent weight/volume 2-amino-2-methyl-1,3-propanediol.

In another embodiment of the instant invention, the electrophoretic gel preferably comprises from about 0.4 to about 1.5 percent weight/volume high electroendosmosis agarose; from about 0.001 to about 2 percent weight/volume guar gum; up to 20 percent volume/volume ethylene glycol; up to 0.5 percent weight/volume sodium azide; and a buffer having a pH of from about 7 to about 10. More preferably, the electrophoretic gel of this embodiment of the instant invention comprises from about 0.7 to about 1.2 percent weight/volume high electroendosmosis agarose; from about 0.01 to about 0.1 percent weight/volume guar gum; from about 1 to about 10 percent volume/volume ethylene glycol; from about 0.05 to about 0.15 percent weight/volume sodium azide; and a buffer having a pH of from about 8 to about 9. Optimally, the electrophoretic gel of this embodiment of the instant invention comprises about 1 percent weight/volume high electroendosmosis agarose; about 0.05 percent weight/volume guar gum; about 5 percent volume/volume ethylene glycol; about 0.1 percent weight/volume sodium azide; and the above described buffer.

In a third embodiment of the instant invention, the electrophoretic gel preferably comprises from about 0.4 to about 1.5 percent weight/volume high electroendosmosis agarose; from about 0.01 to about 2 percent weight/volume arabic acid; from about 0.001 to about 2 percent weight/volume guar gum; up to 20 percent volume/volume ethylene glycol; up to 0.5 percent weight/volume sodium azide; and a buffer having a pH of from about 7 to about 10. More preferably, the electrophoretic gel of this embodiment of the instant invention comprises from about 0.7 to about 1.2 percent weight/volume high electroendosmosis agarose; from about 0.5 to about 1 percent weight/volume arabic acid; from about 0.01 to about 0.1 percent weight/volume guar gum; from about 1 to about 10 percent volume/volume ethylene glycol; from about 0.05 to about 0.15 percent weight/volume sodium azide; and a buffer having a pH of from about 8 to about 9. Optimally, the electrophoretic gel of this embodiment of the instant invention comprises about 1 percent weight/volume high electroendosmosis agarose; about 0.75 percent weight/volume arabic acid; about 0.05 percent weight/volume guar gum; about 5 percent volume/volume ethylene glycol; about 0.1 percent weight/volume sodium azide; and the above described buffer.

The electrophoretic gels of the instant invention can be prepared via any technique well known to those skilled in the art. See, for example, Cawley, supra. In general, the gel solution is preprared by mixing the various ingredients present therein while heating the mixture to a temperature of about 80° to about 100° C. The electrophoretic gel can be prepared by either standard molding or casting techniques. The gels can be stored at any convenient temperature, for example from about 2° to about 40° C., preferably from about 15° to about 26° C. It is preferred to store the electrophoretic gels in sealed, plastic trays until ready for use.

Samples can be applied to the electrophoretic gels of the instant invention via any technique used in the prior art, e.g., via a microliter syrings. The electrophoretic gels can be electrophoresed at 100 volts for 20 minutes. The gels are next incubated at an appropriate temperature, e.g., room temperature to about 50° C., for a convenient period of time, e.g., for up to about two hours, with any known substrate capable of reacting with the LD enzymes present therein. If desired, the gels can be rinsed in an acetic acid solution (5%). In addition, the gels can optionally be dried at about 80° to about 90° C.

The following examples are provided for the purpose of further illustration only and are not intended to be limitations on the disclosed invention.

EXAMPLE 1

The four electrophoretic gel formulations set forth in Table I were each employed in the following protocol in order to demonstrate the improved electrophoretic technique of the instant invention for separating LD isoenzymes and the improved electrophoretic gel for use therein. The sole difference between the four electrophoretic gels employed in this comparative experiment was that the electrophoretic gels within the scope of this invention contained either arabic acid, i.e., a specific acid polysaccharide, and/or guar gum whereas the electrophoretic gel outside of the scope of this invention was devoid of both an acid polysaccharide and a galactomannan polysaccharide.

Protocol

Electrophoretic Procedure

1. A control serum was applied to each gel via a template technique.
2. Gels were electrophoresed at 100 volts for 20 minutes.
3. A standard colorimetric LD substrate was applied to the gels and each gel was incubated at 45° C. for 30 minutes.
4. Gels were soaked in 5% acetic acid and dried at 80°–90° C.
5. Gels were scanned in a densitometer at 600 nm. The results obtained from the above protocol for each gel formulation of Table I are shown in FIGS. 1–4, respectively.

TABLE I

| Formulation | Gel Outside Scope of Invention | Electrophoretic Gels Within Scope of Invention | | |
|---|---|---|---|---|
| | 1 | 2 | 3 | 4 |
| Ingredients | | | | |
| 1% wt/v HE Agarose | X | X | X | X |
| 0.75% wt/v Arabic Acid | | X | | X |
| 0.05% wt/v Guar Gum | | | X | X |
| 0.1% wt/v Sodium Azide | X | X | X | X |
| 0.3% wt/v Aspartic Acid | X | X | X | X |
| 0.4% wt/v Bicine | X | X | X | X |
| 0.3% wt/v Sodium Barbital | X | X | X | X |
| 0.4% wt/v 2-Amino-2-methyl-1,3-propanediol | X | X | X | X |

As shown in FIG. 1, an electrophoretic technique for separating LD isoenzymes employing a prior art electrophoretic gel devoid of both an acid polysaccharide (wherein the acid moiety thereof comprises at least one carboxyl group) and a galactomannan polysaccharide yields an LD isoenzyme pattern having a significant shoulder or bump at the leading edge of the $LD_1$ band. In contrast, an electrophoretic technique for separating LD isoenzymes employing any one of three different embodiments of this invention's improved electrophoretic gel greatly reduces this shoulder or bump on the leading edge of the $LD_1$ band.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. An electrophoretic gel of the type comprising a polysaccharide, characterized in that said electrophoretic gel further comprises a galactomannan polysaccharide.

2. The electrophoretic gel of claim 1 wherein said galactomannan polysaccharide is selected from a group consisting of guar gum and locust bean gum.

3. The electrophoretic gel of claim 1 wherein said galactomannan polysaccharide is guar gum.

4. The electrophoretic gel of claim 1 further comprising a buffer having a basic pH.

5. The electrophoretic gel of claim 4 wherein said galactomannan polysaccharide is selected from a group consisting of guar gum and locust bean gum.

6. The electrophoretic gel of claim 5 wherein said galactomannan polysaccharide is guar gum.

7. The electrophoretic gel of claim 4 further comprising a preservative.

8. The electrophoretic gel of claim 7 wherein said galactomannan polysaccharide is selected from a group consisting of guar gum and locust bean gum.

9. The electrophoretic gel of claim 7 wherein said galactomannan polysaccharide is guar gum.

10. The electrophoretic gel of claim 4 further comprising an alkypolyol having 2 to 6 carbon atoms and 2 to 4 hydroxyl groups.

11. The electrophoretic gel of claim 10 wherein said galactomannan polysaccharide is selected from a group consisting of guar gum and locust beam gum.

12. The electrophoretic gel of claim 10 wherein said galactomannan polysaccharide is guar gum.

13. The electrophoretic gel of claim 4 further comprising a preservative and an alkylpolyol having 2 to 6 carbon atoms and 2 to 4 hydroxyl groups.

14. The electrophoretic gel of claim 13 wherein said polysaccharide is selected from a group consisting of agar and agarose.

15. The electrophoretic gel of claim 14 wherein said preservative is sodium azide and said alkylpolyol is ethylene glycol.

16. The electrophoretic gel of claim 13 wherein said buffer has a pH of from about 7 to about 10.

17. The electrophoretic gel of claim 13 wherein said polysaccharide is selected from a group consisting of agar and agarose; said preservative is sodium azide; said alkylpolyol is ethylene glycol; and said buffer has a pH of from about 7 to 10.

18. The electrophoretic gel of claim 17 wherein said galactomannan polysaccharide is selected from a group consisting of guar gum and locust bean gum.

19. The electrophoretic gel of claim 17 wherein said galactomannan polysaccharide is guar gum.

20. The electrophoretic gel of claim 17 wherein said polysaccharide is high electroendosmosis agarose.

21. The electrophoretic gel of claim 17 wherein said buffer has a pH of from about 8 to about 9.

22. The electrophoretic gel of claim 17 wherein said polysaccharide is high electroendosmosis agarose; and said buffer has a pH of from about 8 to about 9.

23. The electrophoretic gel of claim 22 wherein said galactomannan polysaccharide is selected from a group consisting of guar gum and locust bean gum.

24. The electrophoretic gel of claim 22 wherein said galactomannan polysaccharide is guar gum.

25. The electrophoretic gel of claim 13 comprising:
(a) from about 0.4 to about 1.5% weight/volume high electroendosmosis agarose;
(b) from about 0.001 to about 2% weight/volume guar gum;
(c) up to 0.5% weight/volume sodium azide;
(d) up to 20% volume/volume ethylene glycol; and
(e) a buffer having a pH of from about 7 to about 10.

26. The electrophoretic gel of claim 13 comprising:
(a) from about 0.7 to about 1.2% weight/volume high electroendosmosis agarose;
(b) from about 0.01 to about 1% weight/volume guar gum;
(c) from about 0.05 to about 0.15% weight/volume sodium azide;
(d) from about 1 to about 10% volume/volume ethylene glycol; and
(e) a buffer having a pH of from about 8 to about 9.

27. The electrophoretic gel of claim 13 comprising:
(a) about 1% weight/volume high electroendosmosis agarose;
(b) about 0.05% weight/volume guar gum;
(c) about 0.1% weight/volume sodium azide;
(d) about 5% volume/volume ethylene glycol; and
(e) a buffer having a pH of about 8.2 and comprising about 0.3% weight/volume aspartic acid, about 0.4 weight/volume bicine, about 0.3% weight/volume sodium barbital, and about 0.4% weight/volume 2-amino-2-methyl-1,3-propanediol.

28. An improved electrophoretic technique for assaying the relative distribution of lactate dehydrogenase isoenzymes of the type wherein a sample to be assayed is applied to an electrophoretic gel and said electrophoretic gel is electrophoresed, characterized in that said electrophoretic gel is the electrophoretic gel of any one of claims 1–26 or 27.

29. The electrophoretic gel of claim 1 further comprises an acid polysaccharide and salts thereof, wherein the acid moiety of said acid polysaccharide comprises at least one carboxyl group.

30. The electrophoretic gel of claim 29 wherein said acid polysaccharide is selected from a group consisting of arabic acid, tragacanth acid, khaya acid, alginic acid, pectic acid, and linseed acid and said galactomannan polysaccharide is selected from a group consisting of guar gum and locust bean gum.

31. The electrophoretic gel of claim 30 wherein said salts are selected from a group consisting of sodium, potassium, calcium, and magnesium.

32. The electrophoretic gel of claim 29 wherein said acid polysaccharide is arabic acid and said galactomannan polysaccharide is guar gum.

33. The electrophoretic gel of claim 29 further comprising a buffer having a basic pH.

34. The electrophoretic gel of claim 33 wherein said galactomannan polysaccharide is selected from a group consisting of guar gum and locust bean gum.

35. The electrophoretic gel of claim 34 wherein said galactomannan polysaccharide is guar gum.

36. The electrophoretic gel of claim 33 further comprising a preservative.

37. The electrophoretic gel of claim 36 wherein said acid polysaccharide is selected from a group consisting of arabic acid, tragacanth acid, khaya acid, alginic acid, pectic acid, and linseed acid and said galactomannan polysaccharide is selected from a group consisting of guar gum and locust bean gum.

38. The electrophoretic gel of claim 37 wherein said salts are selected from a group consisting of sodium, potassium, calcium, and magnesium.

39. The electrophoretic gel of claim 36 wherein said acid polysaccharide is arabic acid and said galactomannan polysaccharide is guar gum.

40. The electrophoretic gel of claim 33 further comprising an alkylpolyol having 2 to 6 carbon atoms and 2 to 4 hydroxyl groups.

41. The electrophoretic gel of claim 40 wherein said acid polysaccharide is selected from a group consisting of arabic acid, tragacanth acid, khaya acid, alginic acid, pectic acid, and linseed acid and said galactomannan polysaccharide is selected from a group consisting of guar gum and locust bean gum.

42. The electrophoretic gel of claim 41 wherein said salts are selected from a group consisting of sodium, potassium, calcium, and magnesium.

43. The electrophoretic gel of claim 40 wherein said acid polysaccharide is arabic acid and said galactomannan polysaccharide is guar gum.

44. The electrophoretic gel of claim 33 further comprising a preservative and an alkylpolyol having 2 to 6 carbon atoms and 2 to 4 hydroxyl groups.

45. The electrophoretic gel of claim 44 wherein said polysaccharide is selected from a group consisting of agar and agarose.

46. The electrophoretic gel of claim 44 wherein said preservative is sodium azide and said alkylpolyol is ethylene glycol.

47. The electrophoretic gel of claim 44 wherein said buffer has a pH of from about 7 to about 10.

48. The electrophoretic gel of claim 44 wherein said polysaccharide is selected from a group consisting of agar and agarose; said preservative is sodium azide; said alkylpolyol is ethylene glycol; and said buffer has a pH of from about 7 to about 10.

49. The electrophoretic gel of claim 48 wherein said acid polysaccharide is selected from a group consisting of arabic acid, tragacanth acid, khaya acid, alginic acid, pectic acid, and linseed acid and said galactomannan polysaccharide is selected from a group consisting of guar gum and locust bean gum.

50. The electrophoretic gel of claim 49 wherein said salts are selected from a group consisting of sodium, potassium, calcium, and magnesium.

51. The electrophoretic gel of claim 48 wherein said acid polysaccharide is arabic acid and said galactomannan polysaccharide is guar gum.

52. The electrophoretic gel of claim 48 wherein said polysaccharide is high electroendosmosis agarose.

53. The electrophoretic gel of claim 48 wherein said buffer has a pH of from about 8 to about 9.

54. The electrophoretic gel of claim 48 wherein said polysaccharide is high electroendosmosis agarose; and said buffer has a pH of from about 8 to about 9.

55. The electrophoretic gel of claim 54 wherein said acid polysaccharide is selected from a group consisting of arabic acid, tragacanth acid, khaya acid, alginic acid, pectic acid, and linseed acid; and said galactomannan polysaccharide is selected from a group consisting of guar gum and locust bean gum.

56. The electrophoretic gel of claim 55 wherein said salts are selected from a group consisting of sodium, potassium, calcium, and magnesium.

57. The electrophoretic gel of claim 54 wherein said acid polysaccharide is arabic acid and said galactomannan polysaccharide is guar gum.

58. The electrophoretic gel of claim 44 comprising:
 (a) from about 0.4 to about 1.5% weight/volume high electroendosmosis agarose;
 (b) from about 0.1 to about 2% weight/volume arabic acid;
 (c) from about 0.001 to about 2% weight/volume guar gum;
 (d) up to 0.5% weight/volume sodium azide;
 (e) up to 20% volume/volume ethylene glycol; and
 (f) a buffer having a pH of from about 7 to about 10.

59. The electrophoretic gel of claim 44 comprising:
 (a) from about 0.7 to about 1.2% weight/volume high electroendosmosis agarose;
 (b) from about 0.5 to about 1% weight/volume arabic acid;
 (c) from about 0.01 to about 0.1% weight/volume guar gum;
 (d) from about 0.05 to about 0.15% weight/volume sodium azide;
 (e) from about 1 to about 10% volume/volume ethylene glycol; and
 (f) a buffer having a pH of from about 8 to about 9.

60. The electrophoretic gel of claim 44 comprising:
 (a) about 1% weight/volume high electroendosmosis agarose;
 (b) about 0.75 weight/volume arabic acid;
 (c) about 0.5% weight/volume guar gum;
 (d) about 0.1% weight/volume sodium azide;
 (e) about 5% volume/volume ethylene glycol; and
 (f) a buffer having a pH of about 8.2 and comprising about 0.3% weight/volume aspartic acid, about 0.4% weight/volume bicine, about 0.3% weight/volume sodium barbital, and about 0.4% weight/volume 2-amino-2-methyl-1,3-propanediol.

61. An improved electrophoretic technique for assaying the relative distribution of lactate dehydrogenase isoenzymes of the type wherein a sample to be assayed is applied to an electrophoretic gel and said electrophoretic gel is electrophoresed, characterized in that said electrophoretic gel is the electrophoretic gel of any one of claims 29–59 or 60.

62. An electrophoretic gel comprising:
 (a) from about 0.4 to about 1.5% weight/volume high electroendosmosis agarose;
 (b) from about 0.1 to about 2% weight/volume arabic acid;
 (c) up to 0.5% weight/volume sodium azide;
 (d) up to 20% volume/volume ethylene glycol; and
 (e) a buffer having a pH of from about 7 to about 10.

63. The electrophoretic gel of claim 62 comprising:
(a) from about 0.7 to about 1.2% weight/volume high electroendosmosis agarose;
(b) from about 0.5 to about 1% weight/volume arabic acid;
(c) from about 0.05 to about 0.15% weight/volume sodium azide;
(d) from about 1 to about 10% volume/volume ethylene glycol; and
(e) a buffer having a pH of from about 8 to about 9.

64. The electrophoretic gel of claim 62 comprising:
(a) about 1% weight/volume high electroendosmosis agarose;
(b) about 0.75% weight/volume arabic acid;
(c) about 0.1% weight/volume sodium azide;
(d) about 5% volume/volume ethylene glycol; and
(e) a buffer having a pH of about 8.4 and comprising about 0.3% weight/volume aspartic acid, about 0.4% weight/volume bicine, about 0.3 weight/volume sodium barbital, and about 0.4% weight/volume 2-amino-2-methyl-1,3-propanediol.

65. An improved electrophoretic technique for assaying the relative distribution of lactate dehydrogenase isoenzymes of the type wherein a sample to be assayed is applied to an electrophoretic gel and said electrophoretic gel is electrophoresed, characterized in that said electrophoretic gel is the electrophoretic gel of any one of claims 62–63 or 64.

66. An improved electrophoretic technique for assaying the relative distribution of lactate dehydrogenase isoenzymes of the type wherein a sample to be assayed is applied to an electrophoretic gel and said electrophoretic gel is electrophoresed, characterized in that said electrophoretic gel comprises a polysaccharide, a buffer having a base pH, and an acid polysaccharide and salts thereof, wherein the acid moiety of said acid polysaccharide comprises at least one carboxyl group.

67. The electrophoretic technique of claim 66 wherein said acid polysaccharide is selected from a group consisting of arabic acid, tragacanth acid, khaya acid, alginic acid, pectic acid, and linseed acid.

68. The electrophoretic technique of claim 67 wherein said salts are selected from a group consisting of sodium, potassium, calcium, and magnesium.

69. The electrophoretic technique of claim 66 wherein said acid polysaccharide is arabic acid.

70. The electrophoretic technique of claim 66 wherein said electrophoretic gel further comprises a preservative.

71. The electrophoretic technique of claim 70 wherein said acid polysaccharide is selected from a group consisting of arabic acid, tragacanth acid, khaya acid, alginic acid, pectic acid, and linseed acid.

72. The electrophoretic technique of claim 71 wherein said salts are selected from a group consisting of sodium, potassium, calcium and magnesium.

73. The electrophoretic technique of claim 70 wherein said acid polysaccharide is arabic acid.

74. The electrophoretic technique of claim 66 wherein said electrophoretic gel further comprises an alkylpolyol having 2 to 6 carbon atoms and 2 to 4 hydroxyl groups.

75. The electrophoretic technique of claim 74 wherein said acid polysaccharide is selected from a group consisting of arabic acid, tragacanth acid, khaya acid, alginic acid, pectic acid, and linseed acid.

76. The electrophoretic technique of claim 75 wherein said salts are selected from a group consisting of sodium, potassium, calcium, and magnesium.

77. The electrophoretic technique of claim 74 wherein said acid polysaccharide is arabic acid.

78. The electrophoretic technique of claim 66 wherein said electrophoretic gel further comprises a preservative and an alkylpolyol having 2 to 6 carbon atoms and 2 to 4 hydroxyl groups.

79. The electrophoretic technique of claim 78 wherein said polysaccharide is selected from a group consisting of agar and agarose.

80. The electrophoretic technique of claim 78 wherein said preservative is sodium azide and said alkylpolyol is ethylene glycol.

81. The electrophoretic technique of claim 78 wherein said buffer has a pH of about 7 to about 10.

82. The electrophoretic technique of claim 78 wherein said polysaccharide is selected from a group consisting of agar and agarose; said preservative is sodium azide; said alkylpolyol is ethylene glycol; and said buffer has a pH of from about 7 to about 10.

83. The electrophoretic technique of claim 82 wherein said acid polysaccharide is selected from a group consisting of arabic acid, tragacanth acid, khaya acid, alginic acid, pectic acid, and linseed acid.

84. The electrophoretic technique of claim 83 wherein said salts are selected from a group consisting of sodium, potassium, calcium, and magnesium.

85. The electrophoretic technique of claim 82 wherein said acid polysaccharide is arabic acid.

86. The electrophoretic technique of claim 82 wherein said polysaccharide is high electroendosmosis agarose.

87. The electrophoretic technique of claim 82 wherein said buffer has a pH of from about 8 to about 9.

88. The electrophoretic technique of claim 82 wherein said polysaccharide is high electroendosmosis agarose; and said buffer has a pH of from about 8 to about 9.

89. The electrophoretic technique of claim 88 wherein said acid polysaccharide is selected from a group consisting of arabiac acid, tragacanth acid, khaya acid, alginic acid, pectic acid, and linseed acid.

90. The electrophoretic technique of claim 89 wherein said salts are selected from a group consisting of sodium, potassium, calcium, and magnesium.

91. The electrophoretic technique of claim 89 wherein said acid polysaccharide is arabic acid.

* * * * *